United States Patent [19]

Wright

[11] 4,211,325

[45] Jul. 8, 1980

[54] HEART VALVE HOLDER

[75] Inventor: John T. M. Wright, Huntington Beach, Calif.

[73] Assignee: Hancock Laboratories, Inc., Anaheim, Calif.

[21] Appl. No.: 46,535

[22] Filed: Jun. 7, 1979

[51] Int. Cl.² .................... B65D 85/50; B65D 85/02; B65D 81/24

[52] U.S. Cl. .................................. 206/438; 206/525; 3/1.5

[58] Field of Search ................ 206/438, 525, 527, 18; 3/1.5

[56] References Cited

U.S. PATENT DOCUMENTS

| | | | |
|---|---|---|---|
| 2,880,856 | 4/1959 | Albrecht | 206/438 |
| 3,537,575 | 11/1970 | Haidegger | 206/18 |
| 4,101,031 | 7/1978 | Cromie | 206/438 |

OTHER PUBLICATIONS

The Procurement and Preparation of Aortic Valve Homografts, *Surgery* vol. 62, pp. 839–842, Nov. 1967.

*Primary Examiner*—William T. Dixson, Jr.
*Attorney, Agent, or Firm*—Wayne R. Eberhardt

[57] ABSTRACT

A device for retaining a natural tissue heart valve and stent assembly during storage and transportation prior to implantation of the valve. The device consists of an open-ended, cylindrical valve case having an internal support for a valve support ring adapted to grasp the valve stent. A retainer holds the valve support ring in position within the valve case. The assembled device is stored in a jar containing a preserving liquid until the valve is to be implanted.

17 Claims, 4 Drawing Figures

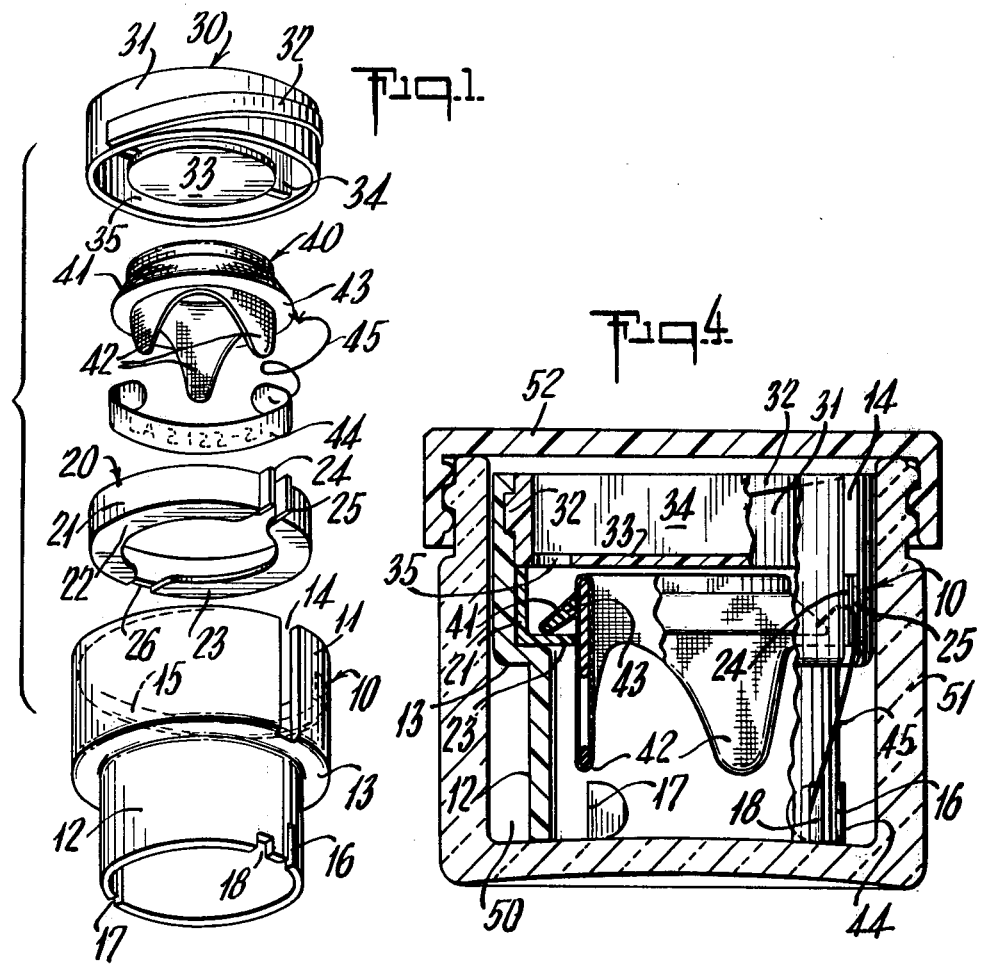

HEART VALVE HOLDER

BACKGROUND OF THE INVENTION

This invention pertains to a device for storing and retaining a natural tissue heart valve, and, more particularly, to a device for retaining a natural tissue heart valve mounted on a valve stent and ready for implantation.

Heart valves taken from pigs and suitably processed are used for implantation in human patients. These heart valves are mounted on a cloth covered framework known as a stent which includes a cylindrical base with three projecting commissure support struts to hold the margins of the cusps of the heart valve. From the base of the stent includes an exterior a sewing ring for suturing into the annulus of the patient when installing the porcine valve in place of the removed diseased valve.

Prior to implantation, the heart valve is treated with a glutaraldehyde solution to preserve the tissue. After mounting in the stent, the valve is stored in a jar or other container of glutaraldehyde solution until such time as the valve is needed for implantation. To protect the valve during storage, it is generally immobilized by means of a packing of rayon or other fibrous material which may include rayon balls inserted into the cusps of the heart valve, frequently with a gauze wrapping around the valve. When the valve is to be used, it is necessary to remove this packing material and to rinse the valve to remove the glutaraldehyde solution. Despite thorough rinsing and washing there is a possibility that some fiber of the packing may be retained on the valve. The presence of fibers or other foreign materials on the valve at the time of implantation can result in clotting and present a danger to the patient.

It is accordingly an object of the present invention to provide a valve holder and retaining device which assures the safe storage and transportation of the tissue heart valve. It is a further object to provide a storage device in which the valve is protected from foreign material. It is a yet further object of this invention to provide a valve holder and storage device which allows the valve to be rinsed and prepared for implantation with a minimum of handling or manipulation. These and other objects of this invention will be readily apparent from the following description.

SUMMARY

The present invention provides a valve holder for retaining a natural tissue heart valve which as been mounted on a valve stent and is ready for implantation. The holder comprises an open-ended, cylindrical case having internal valve support means intermediate the ends of the case, a valve support ring adapted to circumscribe and grasp the heart valve stent and to be retained on the valve support means of the case, and a retainer to secure the valve support ring and valve within the case. The assembled valve holder is immersed in a preservative fluid within a closed container for storage and transportation.

The valve holder is preferably constructed of polypropylene or other inert material which can be molded or machined to the desired configuration. The container of preservative liquid is sized to accept the assembled valve holder with a minimum of vertical and lateral clearance so that the holder is essentially immobilized within the container. The retainer of the valve holder assembly includes handle means for grasping the holder to facilitate removal from the container and rinsing prior to removing the valve for implantation.

DESCRIPTION OF DRAWINGS

FIG. 1 is an exploded view in perspective illustrating the components of the valve holder and their relationship to the heart valve stent.

FIG. 2 is a top plan view of the valve support ring illustrated in FIG. 1.

FIG. 3 is a top plan view of the valve retainer illustrated in FIG. 1.

FIG. 4 is a side view in partial cross section showing the device of FIG. 1 assembled and contained in a storage jar.

DESCRIPTION OF PREFERRED EMBODIMENTS

Referring now to FIG. 1, the heart valve holder of the present invention consists of an open-ended, cylindrical case 10, a valve support ring 20, and a retainer member 30.

Case 10 comprises an upper cylindrical section 11 of a first diameter, and a lower cylindrical section 12 of a second and smaller diameter joined by annular flange 13. Cylindrical section 11 is provided with open lateral slot 14 and internal screw thread 15, the functions of which are explained below. Cylindrical section 12 is optionally provided with slot 18 which serves as an air vent, and slots 16 and 17 which serve to hold the valve identification tag as described below.

Valve support ring 20 consists of a split cylinder 21 having a wall of short, vertical dimension and having spaced apart annular flanges 22 and 23 extending inward from the base of the cylinder wall as illustrated in FIG. 2. The height of cylinder wall 21 is sufficient to project slightly above the top of the valve stent in the assembled holder as described more fully below. Tabs 24 and 25 extend outward from the wall of the cylinder along the split. Section 26 of the cylinder wall located opposite the split does not support a flange and functions as a hinge to allow the valve support ring to be opened and closed.

The outside diameter of valve support ring 20 corresponds to the inside diameter of cylindrical section 11 of case 10 so that the valve support ring is readily inserted within said case. The diameter of the circular opening inside flanges 22 and 23 of the valve support ring indicated as dimension a in FIG. 2 is sized according to the diameter of the valve to be held by the ring. Valve support rings of a fixed outside diameter are accordingly provided with a range of effective inside diameters by varying the width of flanges 22 and 23 in order to accommodate valve and stent assemblies of different sizes.

Retainer 30 illustrated in FIGS. 1 and 2 consists of a short, cylindrical wall 31 having an outside diameter corresponding to the inside diameter of section 11 of case 10 and provided with an external screw thread 32 adapted to cooperate with internal screw thread 15 of case 10. Retainer 30 is further provided with disc 33 affixed to transverse handle member 34 which spans the inside diameter of cylinder 31 and protects the valve in the assembled holder against the possibility of an instrument being thrust into the valve when handling the valve holder. Handle 34 is inset from the base of cylinder 31 by an amount equal to the thickness of disc 33 so that the lower surface of disc 33 is flush with the base of cylindrical wall 31. Annular opening 35 between cylinder 31 and disc 33 as indicated in FIG. 2 is provided to facilitate immersion of the assembled valve holder in the preservative solution during storage and rinsing when the holder is subsequently removed from the storage solution.

Also included in FIG. 1 is heart valve stent 40 which is shown for purposes of illustrating the relative positioning of the valve and the components of the valve holder. Stent 40 consists of annular ring 41 from which three commissure support struts 42 extend. The porcine tissue valve (not shown) is mounted within the confines of the stent by stitching the valve to the cloth-covered stent with the three cusps of the valve oriented to the three struts of the stent. The stent further includes sewing ring 43 which is conventionally a fabric covered ring of silicone foam or other resilient material sewn to the stent between ring 41 and the inner arches of the commissure support struts. Valve stent 40 also includes valve identification tag 44 attached to the sewing ring of the valve by means of thread 45.

The assembly of the heart valve holder and valve stent of FIG. 1 is illustrated in FIG. 4 which shows the assembled valve immersed in preservative fluid 50 and contained in jar 51 sealed with screw cap 52.

Referring now to FIG. 1 and FIG. 4, the valve holder is assembled by first placing valve stent 40 in valve support ring 20 with the struts of the stent extending through the ring opening formed by the flanges of the support ring. The support ring is opened to receive the valve by flexing at hinge 26, and the valve is inserted through the ring so that sewing ring 43 is resting upon the upper surface of flanges 22 and 23. The support ring is then closed so that the stent is grasped by the inner edges of flanges 22 and 23 around the periferal surface between the sewing ring and the upper arches of the struts. The stent is thereby firmly but gently retained within the valve support ring.

The valve stent and supporting ring are next inserted into cylindrical section 11 of case 10 with tabs 24 and 25 of the ring aligned with slot 14 of the case until the supporting ring rests on annular flange 13. Retainer 30 is next inserted in section 11 of case 10 and secured in place over support ring 20 by means of screw threads 15 and 32. Retainer 30 bears on wall 21 of support ring 20 with disk 33 spaced slightly apart from the upper extremity of the heart valve stent. Stent identification tag 44 affixed to stent 40 is finally attached to case 10 by inserting the ends of the tag through slots 16 and 17 to complete the assembly.

The assembled holder is picked up by grasping handle member 34 of retainer 30 with a forceps and placing the entire assembly in jar 51 which contains liquid preservative 50, and which is subsequently closed by means of screw cap 52. Protective disk 33 guards against the forceps inadvertently slipping into the holder and damaging the valve. Any air trapped under the valve is removed by inverting the closed container to release the air bubble through slot 18.

To remove the valve from the holder for implantation, the valve holder assembly and valve are first removed from jar 50 by grasping handle member 34 of the retainer, and the entire assembly is rinsed in distilled water or saline solution to remove the preservative solution. After rinsing, the retainer is removed from the valve holder and the valve and valve support ring are lifted from the case. The valve is removed from the support ring by spreading tabs 24 and 25 to open the ring at hinge 26 to release the valve. After final rinsing, the identification tag is removed from the valve and the valve is ready for implantation.

While the foregoing has described a preferred embodiment of the valve holder of the present invention, it will be appreciated that several variations in design and construction are possible and within the scope of the present invention. For example, while case 10 is illustrated as a larger and smaller cylinder joined by annular flange 13 which functions as a support for the valve support ring, the case could as readily consist of a single cylinder of uniform diameter with an integral internal flange or other supporting structure functionally equivalent to the flange of 13. The sole requirement is that the cylinder be provided with means to locate and secure the valve and valve support ring within the confines of the cylinder.

Valve support ring 20 may also be modified to include three or more annular flange sections. Optional tabs 24 and 25 may be eliminated without substantially affecting the function of the ring.

In regard to retainer 30, disc 33 may be a solid disc as illustrated or may be provided with small vent openings to facilitate rinsing of the valve before removal from the holder. Screw thread 32 may furthermore be replaced by a bayonnet lock or designed to snap fit with corresponding locking means in case 10. These and other variations which will be apparent to those skilled in the art are encompassed within the scope of the present invention.

The holder of the present invention is preferably molded of a semirigid plastic material such as polypropylene, but other inert plastics or metals may be used. The container for the holder assembly is preferably a glass jar which permits visual inspection of the valve holder and the valve identification tag. The liquid medium in the container is preferably a preserving and sterilizing solution such as 0.2 percent aqueous glutaraldehyde.

What is claimed is:

1. A device for holding a natural tissue heart valve stent assembly comprising
   an outer case comprising an open-ended cylinder having integral internal valve supporting means;
   a valve support ring insertable within said outer case to rest on said internal supporting means and adapted to grasp the valve stent around the outer periphery thereof; and
   a retainer securable to said outer case with said valve support ring contained between said retainer and said internal valve supporting means of said case.

2. The device of claim 1 wherein said valve supporting means of said outer case comprises an inwardly extending internal flange.

3. The device of claim 1 wherein said open-ended cylinder has a first section of an inside diameter sufficient to receive said valve support ring, and a second section of a lesser diameter insufficient to receive said valve support ring, said first and second sections being joined by an annular flange forming said internal valve support ring means.

4. The device of claim 1 wherein said valve support ring comprises a cylindrical wall section having a flange extending inwardly from one end thereof, said flange defining an opening of reduced diameter corresponding to the outer diameter of said stent.

5. The device of claim 4 wherein said cylindrical wall section is split, and said flange is discontinuous about the inner periphery of said cylindrical wall.

6. The device of claim 5 wherein said support ring includes tabs projecting outwardly along the split in said cylindrical wall section.

7. The device of claim 1 wherein said retainer comprises a cylindrical wall section insertable in and securable to the open-ended cylinder of said outer case.

8. The device of claim 7 wherein said retainer and said case include cooperating screw threads whereby said retainer is securable in said case.

9. The device of claim 7 wherein said retainer includes a handle member extending between the walls and through the center of said cylindrical wall section.

10. The device of claim 9 wherein said retainer includes a disc flush with one end of said cylindrical wall section and secured to said handle member.

11. In combination with a natural tissue heart valve stent assembly including an external sewing ring, commissure support struts and a peripheral surface between said sewing ring and said support struts, a device for holding said heart valve stent assembly comprising
a valve support ring member circumscribing said valve assembly and engaging said stent about said peripheral surface;
an outer case comprising an open-ended cylinder having integral internal support means adapted to support said valve support ring and valve assembly; and
a retainer secured within said outer case and engaging said valve support ring;
whereby said valve support ring and said valve assembly are immobily retained within said outer case between said retainer and said internal support means of said case.

12. The device of claim 11 wherein said valve support ring comprises a cylindrical wall section with a stent engaging flange extending inwardly from the base of said wall.

13. The device of claim 12 wherein said cylindrical wall of said valve support ring is split and said flange is discontinuous about the inner periphery of said wall section.

14. The device of claim 11 wherein said internal support means of said outer case comprise an internally extending annular flange intermediate the ends of said case.

15. The device of claim 11 wherein said retainer comprises a cylindrical member having an outside diameter corresponding to the inside diameter of said outer case.

16. The device of claim 15 wherein said retainer and said cylindrical case include cooperating screw threads for securing said retainer within said cylindrical case.

17. The device of claim 15 wherein said retainer includes handle means extending across the internal diameter of said cylindrical member and a valve cover disc secured to said handle member with the lower surface of said disc flush with the base of said cylindrical member.

* * * * *